(12) United States Patent
Allaire

(10) Patent No.: US 8,523,567 B2
(45) Date of Patent: Sep. 3, 2013

(54) DENTAL IMPLANT BAR SYSTEM

(76) Inventor: Eric Allaire, Thefford-Mines (CA)

( * ) Notice: Subject to any disclaimer, the term of this patent is extended or adjusted under 35 U.S.C. 154(b) by 0 days.

(21) Appl. No.: 12/998,145

(22) PCT Filed: Sep. 22, 2009

(86) PCT No.: PCT/CA2009/001329
§ 371 (c)(1),
(2), (4) Date: Mar. 22, 2011

(87) PCT Pub. No.: WO2010/031188
PCT Pub. Date: Mar. 25, 2010

(65) Prior Publication Data
US 2011/0195379 A1    Aug. 11, 2011

Related U.S. Application Data

(60) Provisional application No. 61/148,074, filed on Jan. 29, 2009.

(30) Foreign Application Priority Data

Sep. 22, 2008 (CA) ..................... 2639721

(51) Int. Cl.
A61C 8/00 (2006.01)
(52) U.S. Cl.
USPC ........................................ 433/174
(58) Field of Classification Search
USPC ............... 433/172–176, 180–183; 606/280, 606/286, 288–291; 623/17.17
See application file for complete search history.

(56) References Cited

U.S. PATENT DOCUMENTS

| 2,411,001 | A | * | 11/1946 | Rothkranz | .................... 433/182 |
| 5,219,286 | A | | 6/1993 | Hader | |
| 5,286,196 | A | | 2/1994 | Brajnovic et al. | |
| 5,567,155 | A | * | 10/1996 | Hansen | ......................... 433/172 |
| 5,630,717 | A | | 5/1997 | Zuest et al. | |
| 5,885,078 | A | | 3/1999 | Cagna et al. | |
| 5,975,904 | A | | 11/1999 | Spiegel | |
| 6,692,254 | B1 | | 2/2004 | Kligerman et al. | |
| 6,905,336 | B2 | * | 6/2005 | Summers | ....................... 433/214 |
| 7,021,934 | B2 | * | 4/2006 | Aravena | ........................ 433/173 |
| 7,351,058 | B2 | | 4/2008 | Fore et al. | |
| 7,699,611 | B2 | * | 4/2010 | Feijtel | ............................ 433/173 |
| 2003/0108845 | A1 | | 6/2003 | Giovannone et al. | |
| 2005/0019729 | A1 | * | 1/2005 | Fisher et al. | ................... 433/173 |
| 2007/0281283 | A1 | | 12/2007 | Lundgren | |
| 2007/0298655 | A1 | | 12/2007 | Auderset et al. | |

FOREIGN PATENT DOCUMENTS

| DE | 3524556 A1 | 1/1987 |
| DE | 4211561 A1 | 10/1993 |
| ES | 2201906 A1 * | 3/2004 |
| WO | WO 96/03088 A1 | 2/1996 |
| WO | WO 99/22666 A1 | 5/1999 |
| WO | WO 2008/016917 A2 | 2/2008 |

* cited by examiner

Primary Examiner — Robyn Doan
Assistant Examiner — Matthew Nelson
(74) Attorney, Agent, or Firm — Equinox IP; Franz Bonsang

(57) ABSTRACT

The present invention relates to an adjustable dental implant bar system. There is provided a dental implant bar which can be adjusted and which may have articulated and telescopic arms and which can be further secured to implant heads already installed in the patient's mouth or alternatively on a manufactured model made with computerized surgical simulation software or using a conventional dental printing system with transfers.

22 Claims, 14 Drawing Sheets

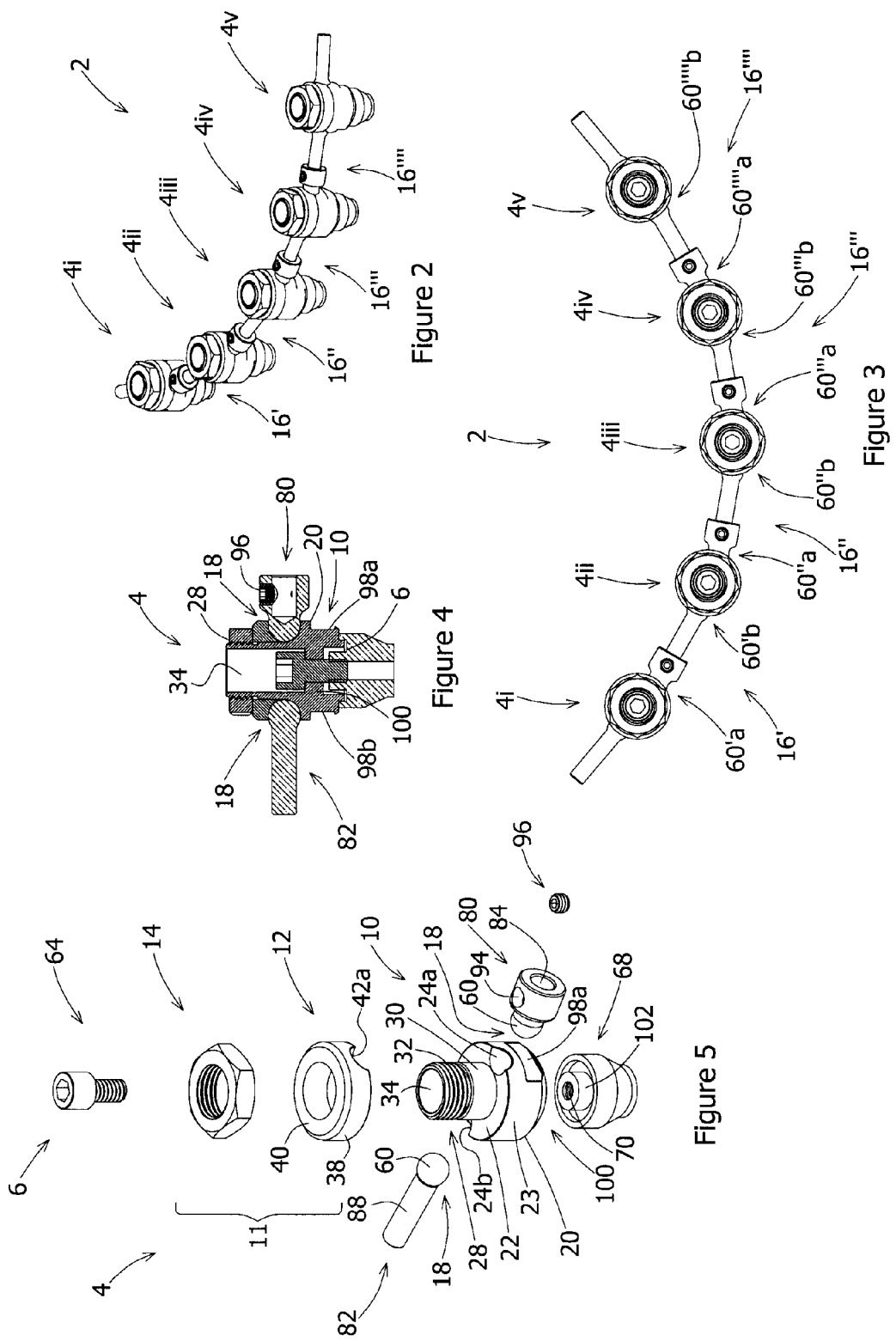

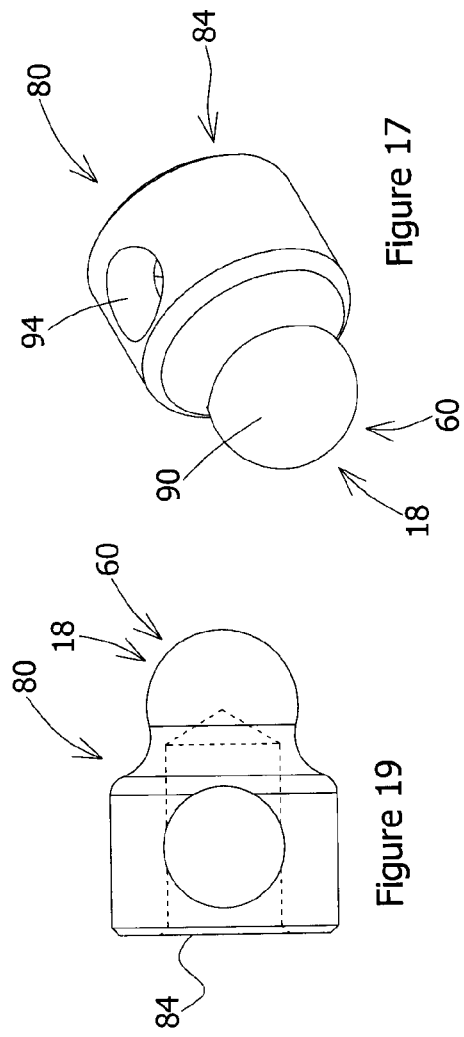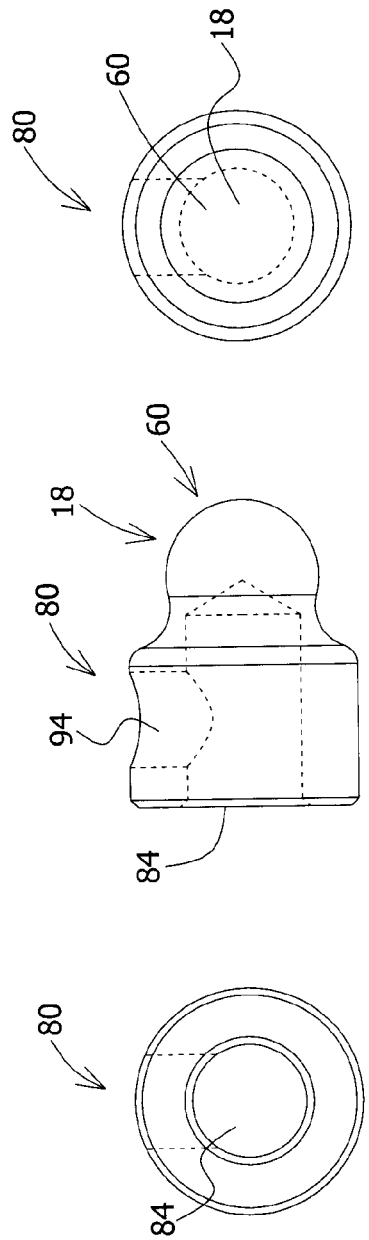

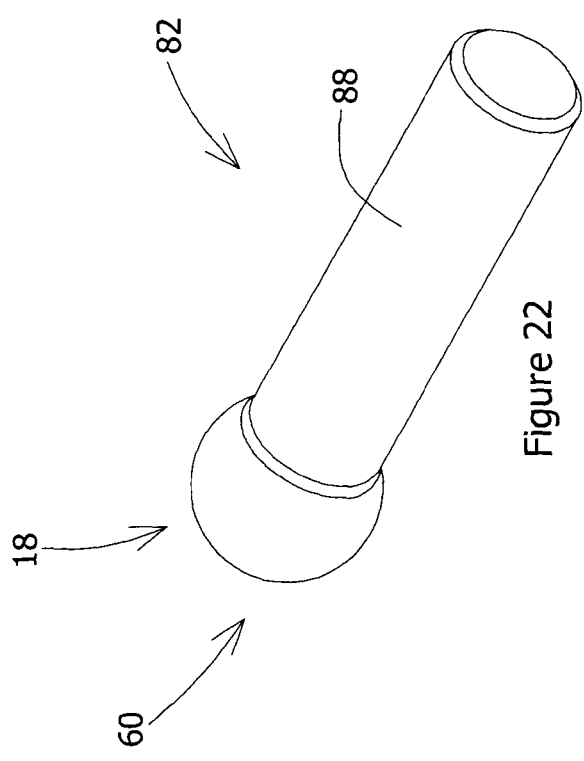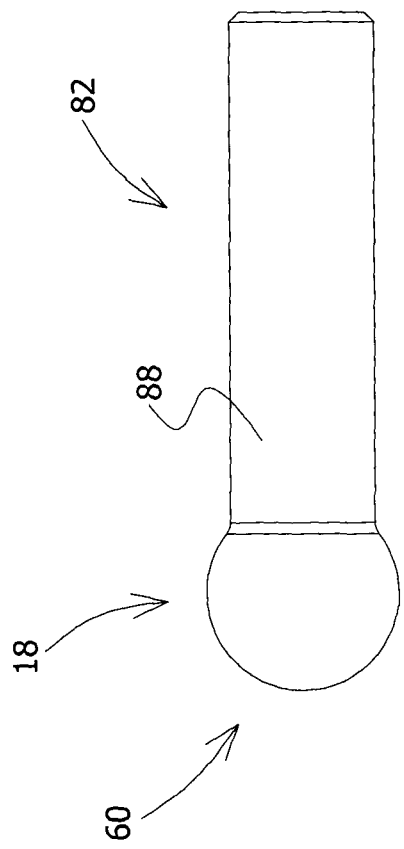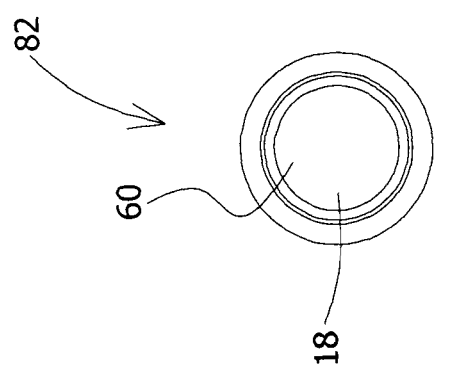

DENTAL IMPLANT BAR SYSTEM

CROSS REFERENCE TO RELATED APPLICATIONS

This application claims the benefits of U.S. provisional application for Patent No. 61/148,074 filed on Jan. 29, 2009, which is herein incorporated by reference.

FIELD OF THE INVENTION

The present invention relates to an adjustable dental implant bar system.

BACKGROUND OF THE INVENTION

Known in the art are dental implant bars and related devices. Dental implants are generally used to provide a base or support for a prosthesis. The implants are placed in the jawbone and act as an anchor point for various dental prosthetic devices. Often, two or more implants are connected together by a dental implant bar, the bar in turn being connected to the dental prosthetic device. Known in the art are, for example, Patent and Patent Application documents No. CA2592538, U.S. 20070190475, DE20221475, SE200402427, U.S. Pat. No. 6,692,254, U.S. 20030108845, NL1017284, U.S. Pat. No. 5,975,904, DE19748268, U.S. Pat. No. 5,885,078, U.S. Pat. No. 5,630,717, CA2195626, DE4211561, EP-534456, SE9100603, DE3524556.

One of the problems of conventional dental implant bars is the amount of time required for fabrication. The use of a lab to fabricate or cast this type of structure is generally required and thus one may encounter delivery delays of up to several weeks.

Moreover, conventional dental implant bars, being fabricated and assembled prior to installation, may be entirely unusable or require considerable modifications if errors occur during the manufacturing process, thus causing additional production delays and costs. The manufacturing of such dental implant bars is generally sub-contracted offsite, increasing costs, delays and risk of error.

Hence, in light of the aforementioned, there is a need for an improved system which, by virtue of its design and components, would be able to overcome some of the above-discussed prior art concerns.

SUMMARY OF THE INVENTION

The object of the present invention is to provide a device which, by virtue of its design and components, satisfies some of the above-mentioned needs and is thus an improvement over other related dental implant bar systems and/or methods known in the prior art. For example, it is an object of the present invention to provide a dental implant bar system which permits adjustment of the same by the dentist or technician.

In accordance with the present invention, the above mentioned object is achieved, as will be easily understood, by a dental implant bar system such as the one briefly described herein and such as the one exemplified in the accompanying drawings.

According to an aspect of the present invention, there is provided a dental implant bar for mounting on a set of prearranged implant heads by an anchoring mechanism and for receiving dental implants. The dental implant bar includes a plurality of implant sockets for receiving the dental implants, each implant socket being adapted to be anchored to a corresponding one of the implant heads by the anchoring mechanism. The dental implant bar further includes at least one adjustable arm assembly, each arm assembly linking an adjacent pair of the implant sockets and each arm assembly having opposite extremities. The dental implant bar further includes at least one compression assembly, each compression assembly being operatively connected to one of the implant sockets, and this, independently with respect to the anchoring mechanism. Each compression assembly holds, against the implant socket, one of the extremities of at least one of the at least one arm assembly linking the corresponding implant socket to an adjacent one of the implant sockets. The compression assembly is operable between a compressed configuration wherein each corresponding extremity is locked against the implant socket and a decompressed configuration wherein each corresponding extremity can swivel to change an orientation of the arm assembly with respect to the implant socket.

According to another aspect of the present invention, there is provided a dental implant system for receiving dental implants. The dental implant system includes a set of prearranged implant heads. The dental implant system further includes a dental implant bar as provided above, each implant socket of the dental implant bar being mounted on one of the prearranged implant heads. The dental implant system further includes an anchoring mechanism for fastening the sockets to the corresponding implant heads.

According to another aspect of the present invention, there is provided a kit for mounting a dental implant bar on a set of prearranged implant heads by an anchoring mechanism and for receiving dental implants. The kit includes a plurality of implant sockets for receiving the dental implants, each implant socket adapted to be anchored to a corresponding one of the implant heads by the anchoring mechanism. The kit further includes at least one adjustable arm assembly, each arm assembly having opposite extremities for linking an adjacent pair of the implant sockets. The kit further comprising at least one compression assembly, each for holding, against one of the implant sockets, one of the extremities of at least one of the at least one arm assembly linking the corresponding implant socket to an adjacent one of the implant sockets, independently with respect to the anchoring mechanism. When the kit is assembled, the compression assembly is operable between a compressed configuration wherein each corresponding extremity is locked against the implant socket and a decompressed configuration wherein each corresponding extremity can swivel to change an orientation of the arm assembly with respect to the implant socket.

According to yet another aspect of the present invention, there is also provided a method for assembling components of the above-mentioned dental implant bar, dental implant system and/or kit.

Embodiments of the present invention provide a dental prosthesis which can be adjusted and which may have articulated and telescopic arms and a dental implant bar which can be secured to implant heads already installed in the patient's mouth or alternatively on a manufactured model made with computerized surgical simulation software or using a conventional dental printing system with transfers. The bar, once adjusted by the dentist, will be integrated in the manufacturing process of an implant support prosthesis.

The objects, advantages and features of the present invention will become more apparent upon reading of the following non-restrictive description of preferred embodiments thereof, given for the purpose of exemplification only, with reference to the accompanying drawings.

BRIEF DESCRIPTION OF THE DRAWINGS

Having thus generally described the invention, reference will be made to the accompanying drawings illustrating embodiments thereof, in which:

FIG. 2 is a perspective view of a dental implant bar assembly according to a second embodiment of the present invention, the bar assembly shown with a plurality of implant bar units linked together.

FIG. 3 is a top view of what is shown in FIG. 2.

FIG. 4 is a cross-sectional side view of an implant bar unit and attached bar assembly according to the second embodiment of the present invention.

FIG. 5 is an exploded view of what is shown in FIG. 4.

FIG. 17 is a perspective view of the ball joint of the bar assembly shown in FIG. 5.

FIG. 18 is a front view of what is shown in FIG. 17.

FIG. 19 is a top view of what is shown in FIG. 17.

FIG. 20 is a right side view of what is shown in FIG. 18.

FIG. 21 is a left side view of what is shown in FIG. 18.

FIG. 22 is a perspective view of the ball pivot arm of the arm assembly shown in FIG. 5.

FIG. 23 is a front view of what is shown in FIG. 22.

FIG. 24 is a right side view of what is shown in FIG. 23.

FIG. 25 is a left side view of what is shown in FIG. 13.

DETAILED DESCRIPTION OF THE INVENTION

Figure 1:
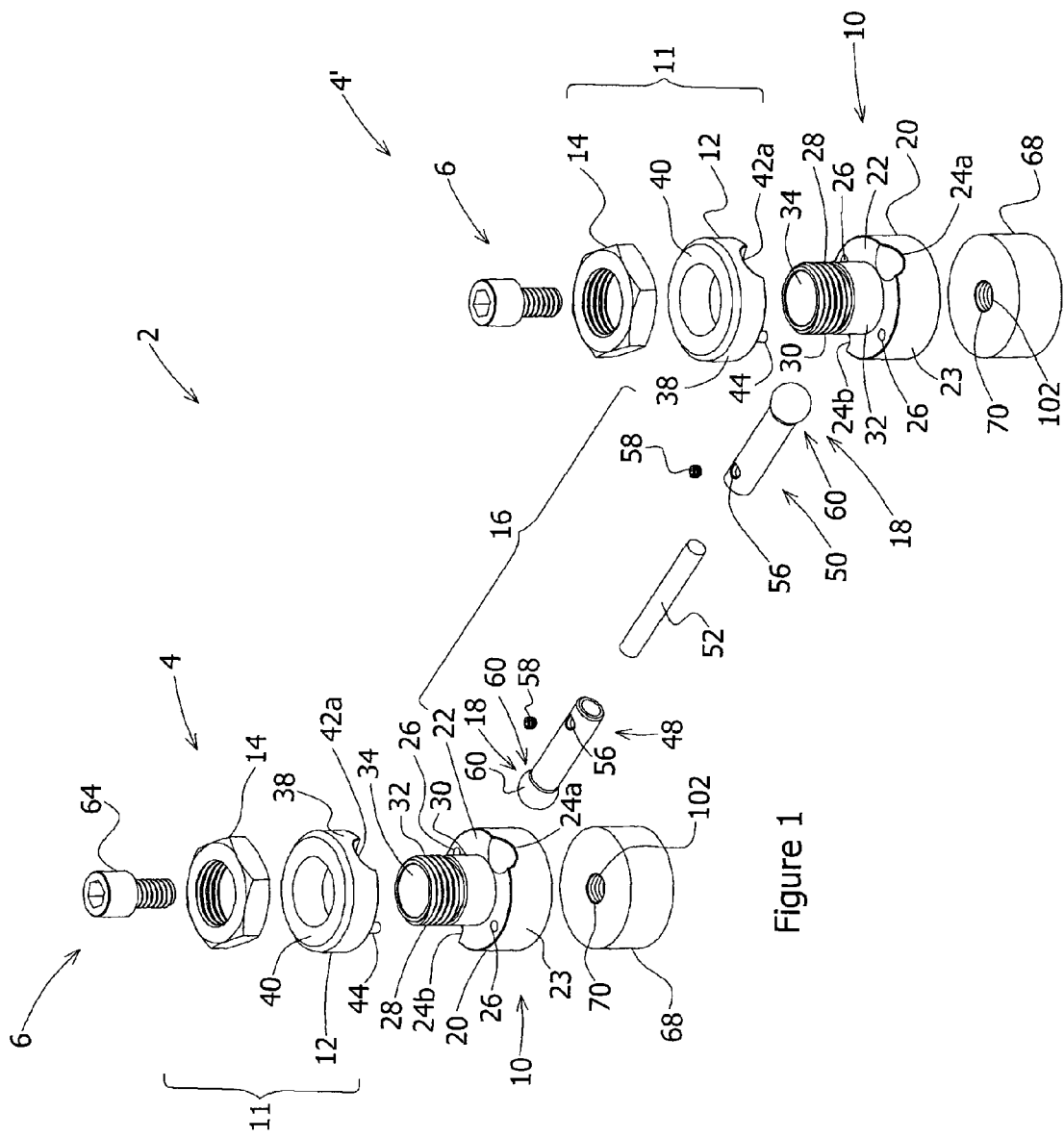
FIG. 1 is a schematic exploded view of a dental implant bar, according to a first preferred embodiment of the present invention.
Figure 7:
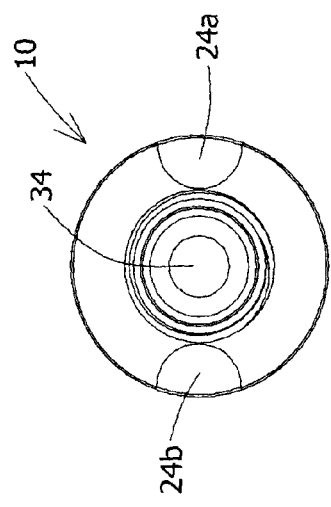
FIG. 7 is a top view of what is shown in FIG. 6.
Figure 6:
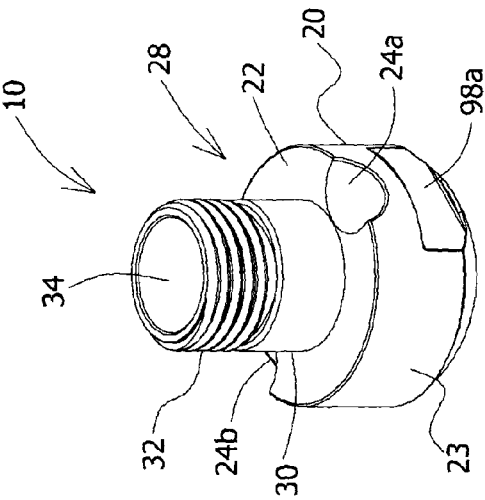
FIG. 6 is a perspective view of the socket of the implant bar unit shown in FIG. 5.
Figure 9:
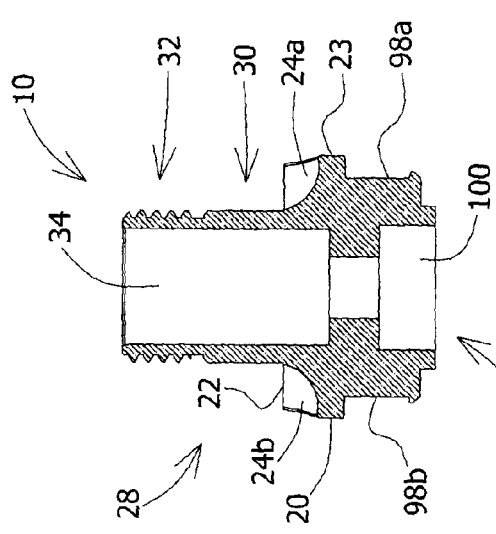
FIG. 9 is a cross-sectional view of what is shown in FIG. 8, taken along line 9-9.
Figure 8:
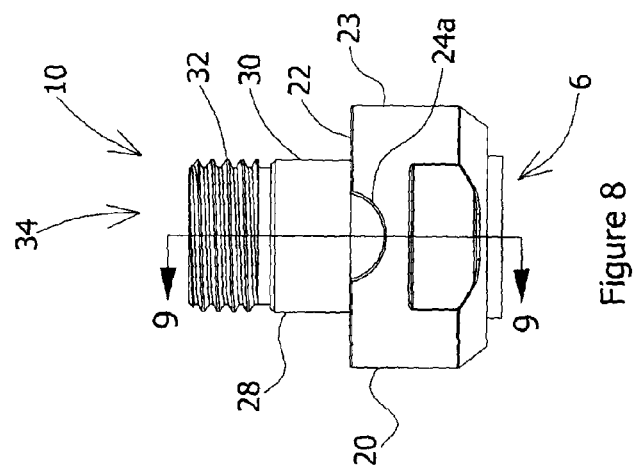
FIG. 8 is a side view of what is shown in FIG. 6.
Figure 13:
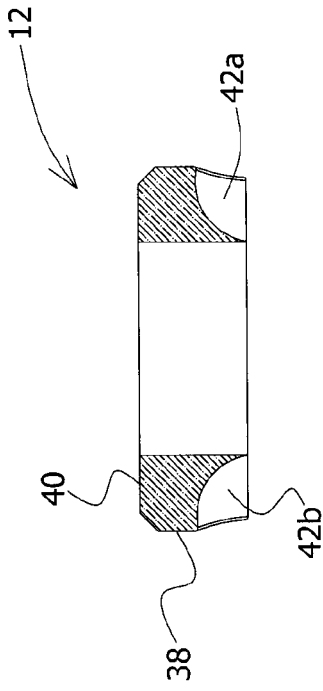
FIG. 13 is a cross-sectional view of what is shown in FIG. 12 along line 13-13.
Figure 11:
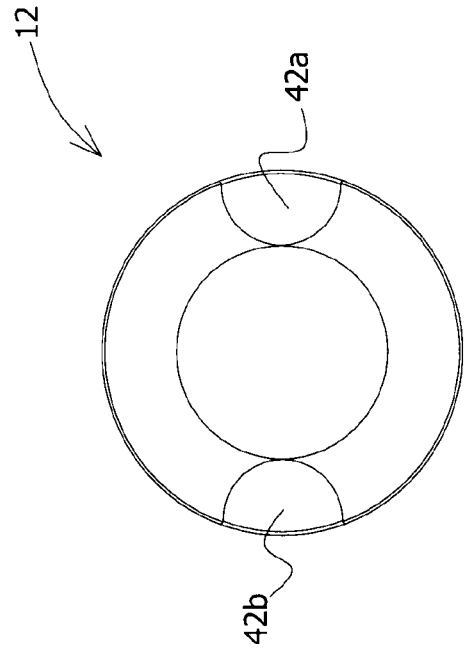
FIG. 11 is a top view of what is shown in FIG. 10.
Figure 12:
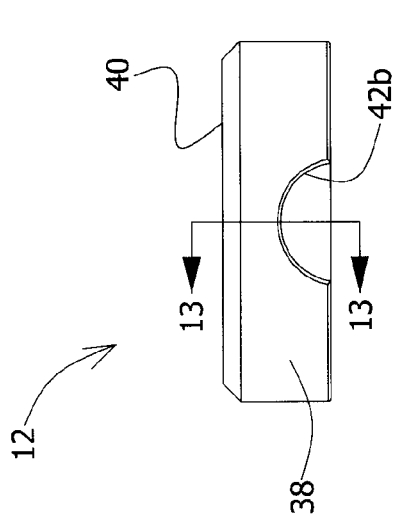
FIG. 12 is a side view of what is shown in FIG. 10.
Figure 10:
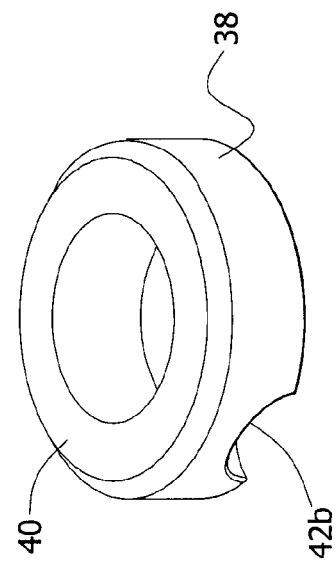
FIG. 10 is a perspective view of the tightening ring of the implant bar unit shown in FIG. 5.
Figure 16:
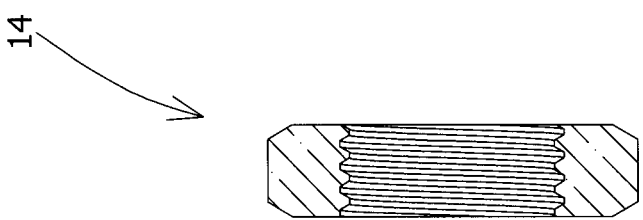
FIG. 16 is a cross-sectional view of what is shown in FIG. 15 along line 16-16.
Figure 15:
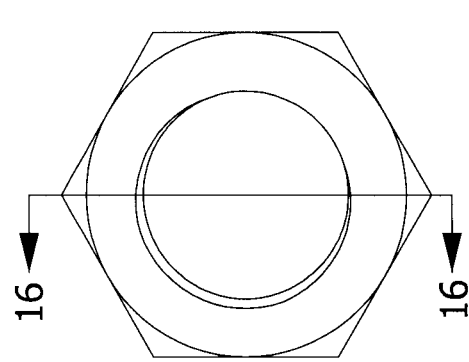
FIG. 15 is a top view of what is shown in FIG. 14.
Figure 14:
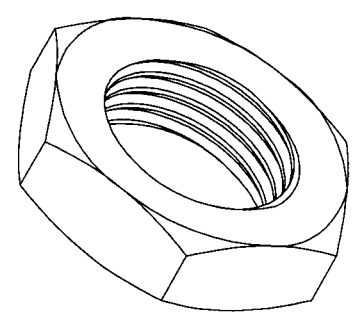
FIG. 14 is a perspective view of the nut of the implant bar unit assembly shown in FIG. 5.
Figure 26:
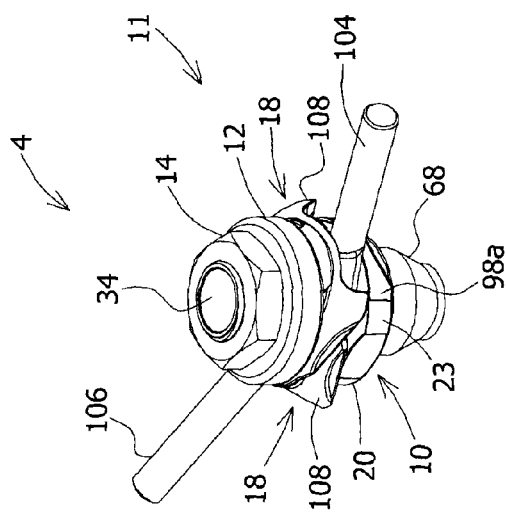
FIG. 26 is a perspective view of a dental implant bar unit according to a third embodiment of the present invention, the bar assembly being shown with a first arm segment of a first arm assembly and a second arm segment of another opposing arm assembly being attached thereto.
Figure 27:
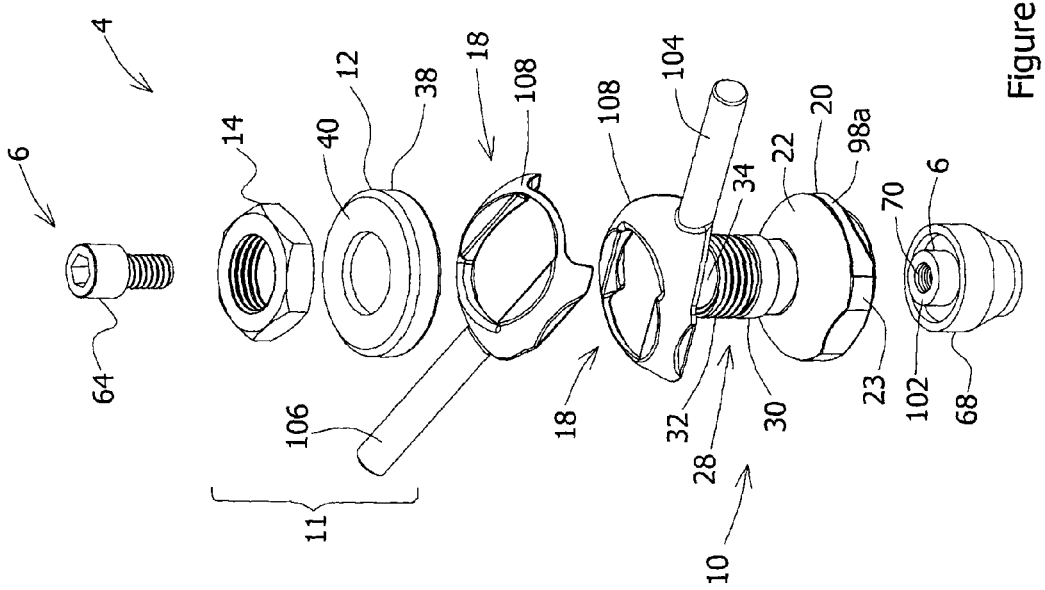
FIG. 27 is an exploded view of what is shown in FIG. 26.
Figure 28:
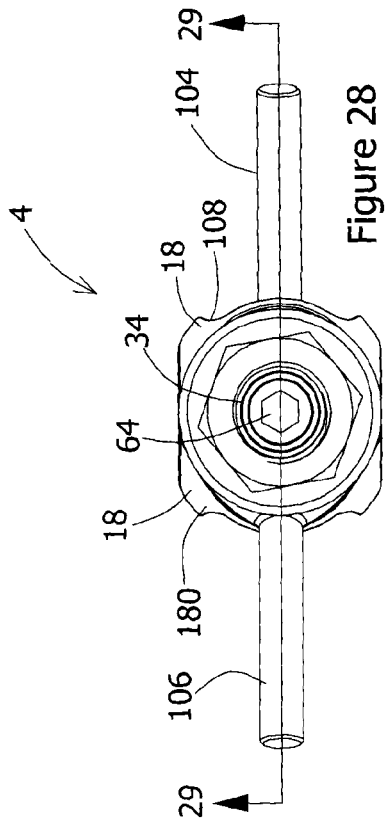
FIG. 28 is a top plan view of what is shown in FIG. 26.
Figure 30:
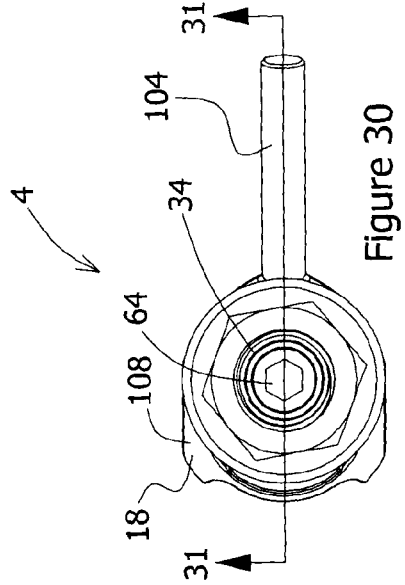
FIG. 30 is a top plan view of what is shown in FIG. 26, the implant bar unit being shown without the second arm segment.
Figure 29:
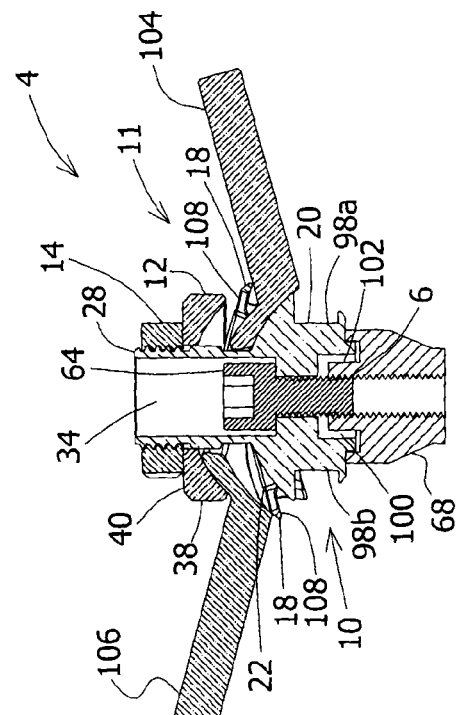
FIG. 29 is a cross-sectional side view of what is shown in FIG. 28, taken along line 29-29.
Figure 31:
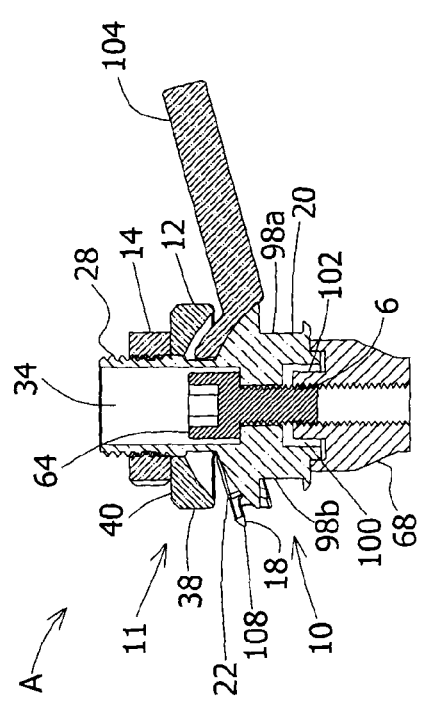
FIG. 31 is a cross-sectional side view of what is shown in FIG. 30, taken along line 31-31.
Figure 32:
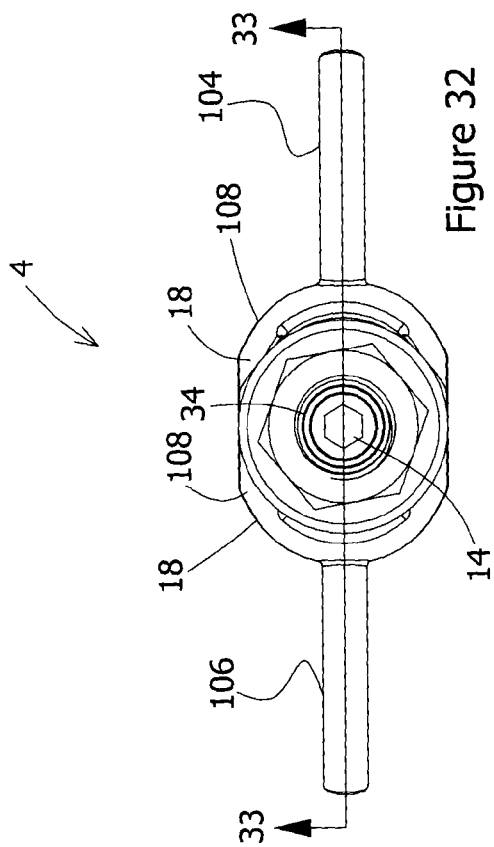
FIG. 32 is a top plan view of what is shown in FIG. 26, the arm assembly being now positioned in a different configuration.
Figure 33:
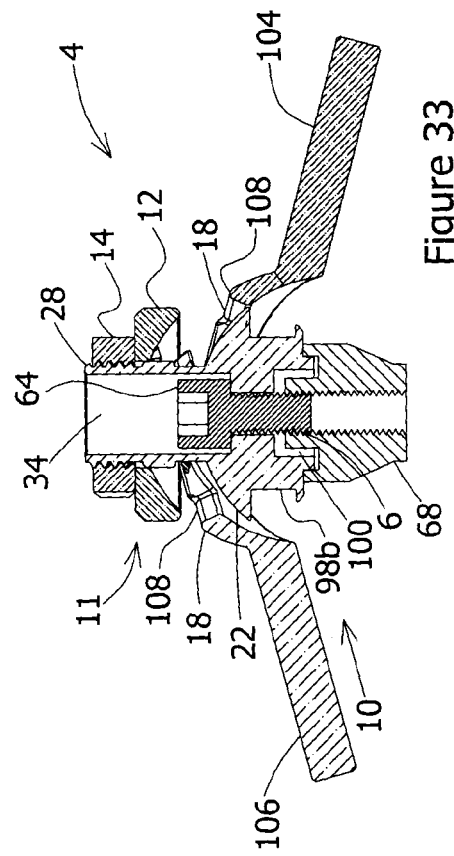
FIG. 33 is a cross-sectional side view of what is shown in FIG. 32, taken along line 33-33.
Figure 34:
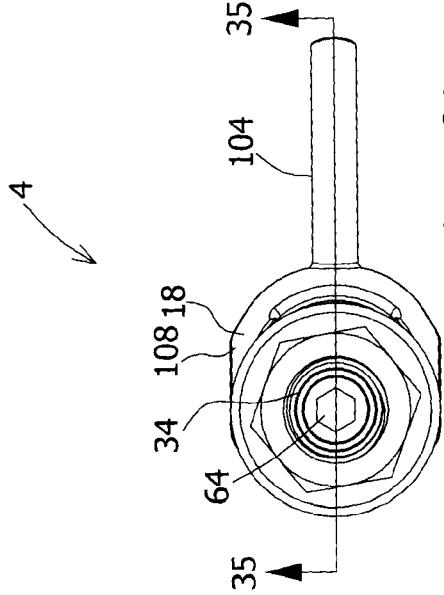
FIG. 34 is a top plan view of what is shown in FIG. 32, the implant bar unit being shown without the second arm segment.
Figure 35:
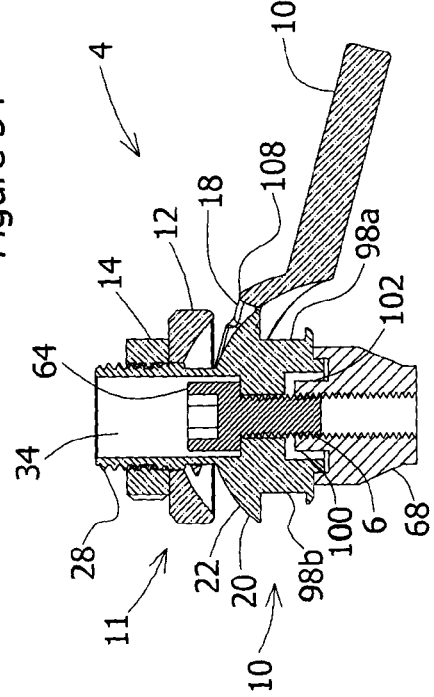
FIG. 35 is a cross-sectional side view of what is shown in FIG. 34, taken along line 35-35.
Figure 39:
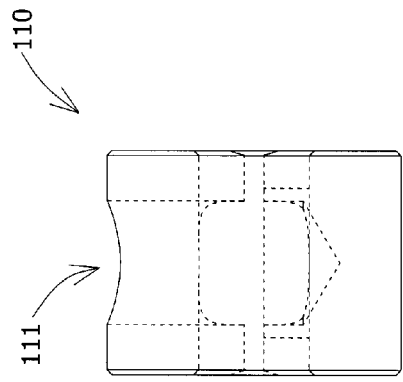
FIG. 39 is a right side view of what is shown in FIG. 36.
Figure 38:
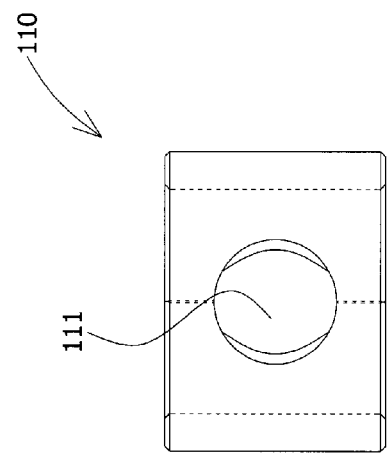
FIG. 38 is a top view of what is shown in FIG. 36.
Figure 37:
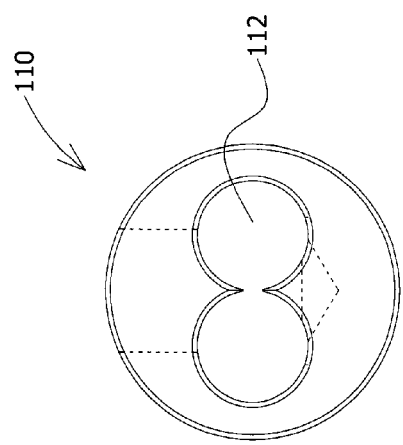
FIG. 37 is a front view of what is shown in FIG. 36.
Figure 36:
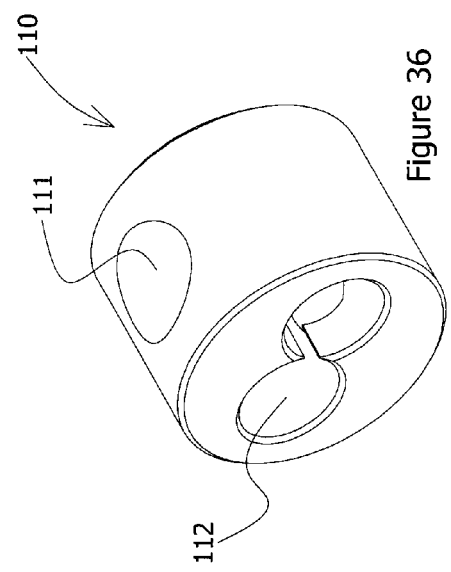
FIG. 36 is a perspective view of an overlapping arm segment.

In the following description, the same numerical references refer to similar elements. The embodiments, geometrical configurations, materials mentioned and/or dimensions shown in the figures or described in the present description are preferred embodiments only, given for exemplification purposes only.

In the context of the present invention, the expressions "fastening", "securing", "engaging", "tightening" and any other equivalent expression known in the art may be used interchangeably. Similarly, the expressions "implant", "implant head" and "post" may be used interchangeably, in the context of the present invention. In addition, although the preferred embodiment of the present invention as illustrated in the accompanying drawings include specific components such as a nut, a self tapping screw, an implant screw, a spherical end, a cylindrical base, a cylindrical extension, a ball pivot arm and ball joint, etc., and although the preferred embodiment of dental implant bar system and corresponding parts thereof consists of certain geometrical configurations as explained and illustrated herein, not all of these components and geometries are essential to the invention and thus should not be taken in their restrictive sense, i.e. should not be taken as to limit the scope of the present invention. It is to be understood, as also apparent to a person skilled in the art, that other suitable components and cooperations thereinbetween, as well as other suitable geometrical configurations may be used for the dental implant bar system according to the present invention, as will be briefly explained herein and as can be easily inferred herefrom, by a person skilled in the art, without departing from the scope of the invention.

According to a first aspect of the invention, there is provided a dental implant bar for mounting on a set of prearranged implant heads by an anchoring mechanism and for receiving dental implants. Referring to the drawings in greater detail and by reference characters thereto, the dental implant bar 2 according to embodiments of the invention includes at least two implant bar units 4, neighboring pairs of implant bar units being linked by an arm assembly generally designated by the reference numeral 16. Each implant bar unit 4 is adapted to be mounted on an implant head 68, for example affixed in the mouth of a patient. As well known in the art, the implant head 68 may for example be provided with a threaded aperture 70 therein, and the anchoring mechanism 6 include a prosthetic screw 64 engaging the threaded aperture 70 and holding component(s) of the implant bar unit 4 therebetween.

Referring to FIGS. 1 to 5, there are shown components of a dental implant bar 2 according to first and second embodiments of the invention. Each dental-implant-bar unit 4 includes an implant socket generally designated by reference numeral 10 and a compression assembly, which is generally designated herein by reference numeral 11. The implant sockets 10 are designed to receive the dental implants, as know by those skilled in the art. Each implant socket 10 is adapted to be anchored to a corresponding implant head 68 by the anchoring mechanism 6.

The dental implant bar 2 further includes at least one adjustable arm assembly 16. Each arm assembly 16 links an adjacent pair of the implant sockets 10 and has opposite extremities 18. Each dental implant unit 4 further includes a compression assembly 11 operatively connected to one of the corresponding implant socket 10 and this, independently with respect to the anchoring mechanism 6. Each compression assembly 11 holds, against the implant socket 10, one of the extremities 18 of each arm assembly 16 linking the corresponding implant socket 10 to an adjacent implant socket. The compression assembly 11 is operable between a compressed configuration wherein each corresponding extremity 18 is locked against the implant socket 10 and a decompressed configuration wherein each corresponding extremity 18 can swivel to change an orientation of the arm assembly 16 with respect to the implant socket 10.

It is an advantageous aspect of the invention that the connection of the compression assembly to the implant socket is independent of the anchoring mechanism; as a result, the compression assembly can remain connected to the implant socket even if the anchoring mechanism is disengaged and the entire dental implant bar removed from the mouth of the patient.

Preferably, the implant socket 10 includes a base 20, typically a lower cylindrical portion, which has a top wall 22 and a side wall 23. A pair of opposed recesses 24a and 24b are formed along the joinder of top wall 22 and side wall 23. Preferably a shaft 28, typically an upper cylindrical portion, projects upwardly from the top wall 22 of the socket 10. The shaft 28 is thus generally sitting on top of the base 20, and as shown in the drawings, is of a smaller diameter than the base 20. The shaft 28 preferably includes a smooth segment 30 and a threaded segment 32. An aperture 34 is provided in a top wall of the shaft 28 which extends through the implant socket. The shaft of the prosthetic screw 64 can therefor be received through this aperture to engage the threaded aperture 70 in the implant head 68. In one variant of this embodiment, best seen in FIGS. 4 and 5, the implant socket 10 further defines a collar 100 in the base 20 in order to receive a complementary connector 102 of the implant head 68, as part of the anchoring mechanism 4 for fastening each socket 10 of the implant bar 2 onto the implant heads 68. The collar 100 communicates with aperture 34.

Preferably, each compression assembly 11 comprises a tightening ring 12 and a nut 14. The tightening ring 12 is sized and shaped for mounting on the base 20 and about the shaft 28 of the implant socket 10. The nut 14 is sized and shaped for mating with the threaded segment 32 of the shaft 28 to hold the tightening ring 12 against the base 20. Preferably, the tightening ring 12 has a side wall 38 and a top wall 40. As will be seen in the drawings, a pair of opposed recesses 42a and 42b is located at the bottom of side wall 38.

According to a first preferred embodiment of the present invention and referring to FIG. 1 of the drawings, arm assembly 16 includes a first arm segment 48 and a second arm segment 50 with a central telescoping segment 52 being located therebetween. The arm segments 48, 50 are substantially identical and positioned substantially symmetrically with respect to the central segment. As may be seen in the drawing, the first arm segment 48 includes a sphere-shaped extremity 60 and a tubular body portion for slidably receiving the central segment therein. Similarly, the second arm segment 50 also includes a sphere-shaped extremity 60. Both, the first 48 and second 50 arm segments are substantially tubular in order to slidably receive the central segment 52 therein from respective ends thereof. The sphere-shaped extremities 60 correspond to extremities 18 of the arm assembly 16, as can be easily understood. Alternatively, each of the first arm segment 48, the central segment 52 and the second arm segment 50 may be of any suitable shape, size and configuration for being slidably connected, typically in a telescoping cooperation.

Alternatively, with further reference to FIGS. 36 to 39, the central segment may be an overlapping segment 110, so as to receive first 48 and second 50 arm segments in an overlapping fashion, in opening 112. Such a configuration allows the arm assembly 16 to be adjustable to a smaller length, in comparison with an arm assembly connected by central segment 52. The overlapping segment 110, preferably provides a threaded aperture 111 for receiving therein a screw which allows to frictionally lock the arm segments therein.

The tubular body portion of each arm segment 48, 50 is further provided with a threaded aperture 56 extending transversely therein. Threaded aperture 56 is designed to receive a screw 58 which allows to frictionally lock the arm segments 48, 50 in a desired position with respect to the central segment 52. Alternatively, such a fastening or locking mechanism may be provided at any suitable location or component depending on the particular configuration of the arm assembly 16. As another alternative, other types of fasteners or fastening mechanism may be provided between the arm segments and telescopic segments without departing from the scope of the invention. The fastening mechanism may further allow adjusting the arm assembly in length or configuration, or even to disassemble the arm assembly, namely by unscrewing the set screw 58, and thereby allowing the central segment 52 to slide with respect to the arm segment 48, 50.

Referring now to FIGS. 2 to 25, according to another embodiment of the present invention, the arm assembly 16 may include an arm segment 82, namely a ball pivot arm (see FIGS. 22 to 25) and a joining mean such as a sleeve 84 projecting from opposite extremities of the arm assembly 16. The arm segment 82 slides into the sleeve 84. The sleeve 84 may include a ball joint 80 (see FIGS. 17 to 21) corresponding to one of the extremities 18 of the arm assembly 16. The arm segment 82 preferably includes a ball end 86, corresponding to the other extremity 18 of the arm assembly 16, and an extension 88. The sleeve 84 is provided with a threaded aperture 94 extending transversely therein, preferably along the extention 88, for receiving a screw 96, which can frictionally lock the arm segment 82 in position with respect to the sleeve 84 or allow changing the length or configuration of the arm assembly, namely by unscrewing the set screw 96 and allowing the arm segment 82 to slide with respect to the sleeve 84.

According to a third embodiment of the present invention, referring now to

FIGS. 26 to 35, the arm assembly 16 may comprise a first arm segment 104 and a second arm segment 106, which are slidably engaged in a telescoping cooperation and project from opposite extremities 18 of the arm assembly 16. The first arm segment and/or the second arm segment may have a threaded aperture extending transversally therein, for receiving a set screw, namely to frictionally lock or to adjust the position of the first arm segment with respect to the second arm segment, similarly to the arm assembly according to the first and second embodiments.

With respect to the connection between of the arm assembly and the implant bar units, the extremity(ies) of each connecting arm assembly is preferably retained by being sandwiched between the implant socket and the compression assembly.

For example, in the illustrated embodiment of FIG. 1, the spherical extremity 60 of the first arm segment 48 is designed to fit within a semispherical recess formed by recesses 24 and 42 of an implant bar unit 4. The second arm segment 50 fits in an identical arrangement on an adjacent implant bar unit 4'. Indeed, the lower-half recesses 24a and 24b provided in the socket 10 and the complementary upper-half recesses 42a and 42b provided in the tightening ring 12 preferably form, when aligned, a corresponding pair of substantially semispherical recesses, each for receiving one of the sphere-shaped extremities 60 of a corresponding arm assembly 16.

More particularly, the spherical extremity 60 of an arm assembly 16 may be nested in the corresponding lower-half recess 24 of the corresponding implant socket 10. The tightening ring, is then mounted onto the base of the socket 10, by aligning the upper-half recess 42 with the lower-half recess 24. To aid in the positioning, locating pins 44 extending from an underside of the tightening ring 12 fit within locating apertures 26 formed in top wall 22 of the base 20 of the implant socket 10. The tightening ring 12 may be compressed against the socket 10 by further introducing nut 14 about the shaft 28 of the implant socket 10, and by a screwing motion of the nut 14 about the threaded segment 32. The spherical end 60 may thus be locked so as to prevent axial or rotational movement of the arm segments 48, 50, thus bringing the compression assembly in a compressed configuration. The tightening ring 12 may be decompressed from the implant socket 10 by unscrewing nut 14, thereby defining a decompressed configuration of the compression assembly and allowing a rotational movement of the arm assembly 16 in order to adjust the orientation thereof. Indeed, the arm assembly 16 can then be rotated in any direction within a suitable range of angles, as can be easily understood, when referring to the drawings.

According to the second embodiment of the present invention and referring now to FIG. 5, sphere-shaped extremity 60 of the sleeve 84 is similarly designed to fit within semispherical recesses formed by recesses 24 and 42 of the implant bar unit 4. The sleeve 84 is further shaped and sized to receive extension 88 of a complementary ball pivot arm 82. The sphere-shaped extremity 60 of the complementary ball pivot arm 82 is also adapted to fit with semispherical recesses 24 and 42 of another implant bar unit. The threaded aperture 94 is designed to receive a screw 96 for securing the extension 88 in place.

Referring back to FIGS. 26 to 35, the extremities 18 of each arm assembly 16 may have a substantially annular shape 108, i.e. ring-shape. Preferably, the extremities 108 of the arm assemblies 16 and the upper wall 22 of the base 20 of each implant socket 10 have mating curved profiles, in order to allow rotational movement of the arm assembly 16 when the compression assembly 11 is configured in a decompressed configuration, as can be better understood when referring to the drawings.

Of course, any of the above-mentioned telescoping cooperations of the arm assembly 16 may be suitably combined with any of the extremities 18 described herein, i.e. sphere-shaped or ring-shaped, as can be easily understood by a person skilled in the art, without departing from the scope of the present invention.

Moreover, the arm assembly 16 may include differently shaped extremities 18 and/or cooperations thereof with the implant bar units 4. For example, according to embodiments of the present invention, the arm assembly 16 may be fixedly secured, at a first extremity $18_1$, to one of the implant bar units 4 (i.e. requiring or without requiring a compression assembly) while being adjustably secured, at a second extremity $18_2$, to another adjacent implant bar unit 4'. Moreover, the first extremity $18_1$ may be adjustably secured to the first implant unit 4, with a smaller range or a more limited range of axial movement relative to the range of movement of the second extremity $18_2$ with respect to the corresponding implant bar unit 4'.

Referring now to FIGS. 2 and 3, a first sphere-shaped extremity 60a' of an arm assembly 16' is received in the corresponding semi-spherical recess provided in implant unit $4_i$. A second sphere-shaped extremity 60b' of the same arm assembly 16' is received in a first semi-spherical recess of another adjacent implant unit $4_{ii}$, thereby linking implant bar units $4_i$, and $4_{ii}$. Moreover, a first sphere-shaped extremity 60" a of a succeeding arm assembly 16" is received in a second semi-spherical recess of the implant unit $4_{ii}$. A second sphere-shaped extremity 60"b of the same arm assembly 16" is then received in a first semi-spherical recess of a subsequent adjacent implant unit $4_{iii}$, thereby linking implant bar units $4_{ii}$ and $4_{iii}$. The next implant bar unit $4_{iv}$, is further linked in the same way by another corresponding arm assemblies 16''' to implant bar unit $4_{iii}$ and so on and so forth. It will be understood that the number of implant bar unit in a given embodiment will be dictated by the number of implants to be provided in the mouth of the corresponding patient, and that in the lower limit two implant sockets linked by a single arm assembly may be provided without departing from the scope of the present invention.

According to an alternative embodiment, the socket 10 and/or the tightening ring 12 of one or more of the implant bar unit 4 may have only one half recess in order to form, when assembled a resulting recess for receiving only one extremity of an arm-assembly, for example if the corresponding implant bar unit is a first or a last unit of the dental implant bar assembly. Alternatively, the socket and/or tightening ring may have any suitable number of such recesses, as can be easily understood by a person skilled in the art.

As previously mentioned and with reference to FIG. 1, a pair of locating apertures 26 are formed in top wall 22 of socket 10, preferably in opposing locations thereon and a pair of corresponding locating pins 44 extends downwardly from the tightening ring 12 to fit within locating apertures 26 of socket 10. Though not illustrated in all the figures, a pair of locating apertures and corresponding pins may be included in other embodiments of the present invention, described herein.

Figure 40:
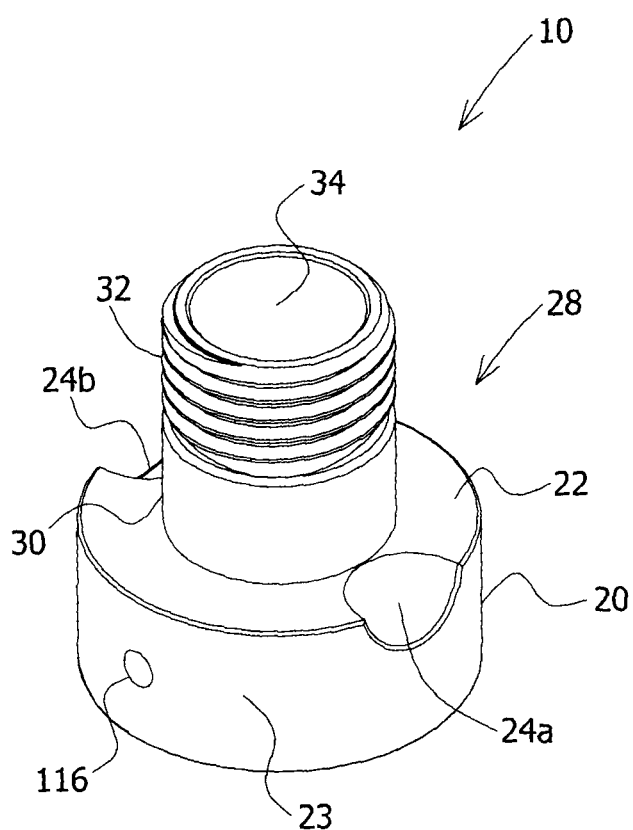
FIG. 40 is a perspective view of a socket of an implant bar system, according to another embodiment of the present invention.

Furthermore, as better illustrated in FIGS. 5 to 9, the implant socket is preferably provided with adjusting means, such as opposed recesses 98a and 98b formed on a lower portion of implant socket 10. By using a suitable gripping tool such as a wrench for rotatably adjusting and/or securing the implant socket 10, the tightening ring 12 may be adjusted, namely by screwing or unscrewing nut 14. Such adjusting means and/or opposed recesses 98a and 98b may be provided on any embodiment of the present invention described herein. Alternatively, referring now to FIG. 40, the adjusting means may include an opening 116 provided in the implant socket, the opening 116 being sized and shaped for receiving a suitable shaft and or the like for adjusting the corresponding socket and/or compression assembly.

With regards to the operational aspect, the implant socket 10 is preferably manufactured in order to fit on implant head or post 68. Implant head or post 68 may or may not form an integral part of implant. The tightening ring 12 is preferably designed to cover smooth segment 30 and extend slightly at the level of the threaded segment 32. The tightening nut 14 compresses the tightening ring 12 against the socket 10, by engaging the threaded segment 12. According to a preferred embodiment, implant screw 64, which may in practice may already be provided as part of an existing implant, passes through aperture 34 and engages threaded aperture 70 in post 68 to fasten the implant socket 10 onto the implant head 68. Alternatively, the implant socket 10 may be fastened on the implant head 68 by any other suitable fastening means, for example a configuration wherein the implant socket 10 and implant head 68 form a push button, etc. or, any other frictional retention means, such as a conical profile as used in the SynCone™ dental implant system.

Figure 41:
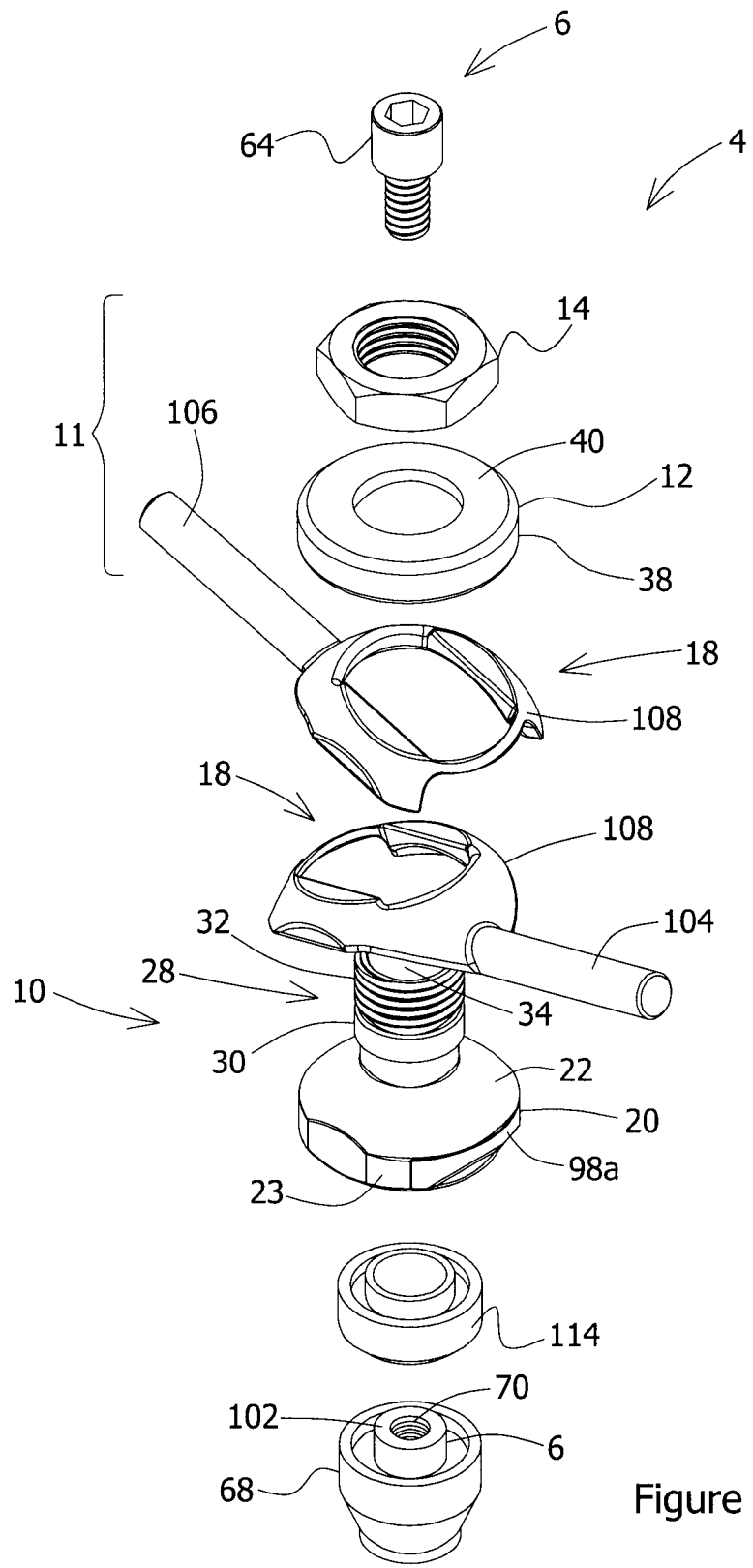
FIG. 41 is another exploded view of what is shown in FIG. 27, the implant bar unit being now shown with an adapter positioned between the socket and the implant head.
Figure 42:
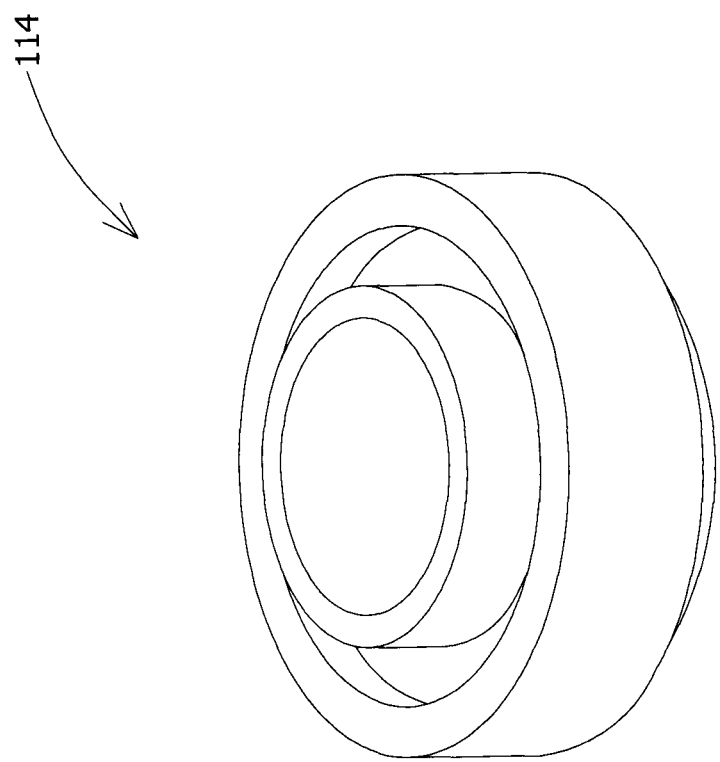
FIG. 42 is a perspective view of the adapter shown in FIG. 41.

Moreover, referring now to FIGS. 41 and 42, the anchoring mechanism of the implant bar may include an adapter 114 operatively connected between the base and the implant head, in order to allow anchoring the implant bar on differently shaped implant heads, either on a model for laboratory or on a patient. Indeed, and as can be easily understood, implant posts and implant heads may be provided in a variety of shapes and may each be provided with different types of connections for receiving an implant bar. The adapter may thus allow anchoring the implant bar on different sets of such prearranged implant heads, so as to render the implant bar system universally compatible with any or at least a wide variety of implant heads or implant posts.

As previously mentioned, the compression assembly 11 is operable independently with respect to the anchoring mechanism. That is to say, while the socket 10 is fastened to the implant head 68 via the prosthetic screw 64, the compression assembly 11 may be added on to the socket, removed therefrom or adjusted by tightening or loosening the ring 12, and this without affecting the cooperation between screw 64 and the implant head 68. Moreover, the compression assembly 11 may be added onto the socket 10, removed therefrom or adjusted similarly, even if the socket 10 is not fastened or placed on the implant head 68. Furthermore, the socket 10 may be connected and/or fastened to the implant head 68 and/or removed therefrom irrespective of the configuration of the socket with respect to the compression assembly.

Embodiments of the present invention are particularly advantageous in that the implant bar may be adjusted, with respect to orientation and length, in certain circumstances, for example, when an implant and/or implant head is replaced or, when the implant bar presents imperfections due to the manufacturing process or due to errors in the printed implant model, thus rendering the implant bar to be reversible or adjustable. Moreover, the dental implant bar, according to the present invention, can be adjusted, locked, and readjusted, at any time. Moreover, the compression assembly, which allows assembly of the dental bar via the arm assemblies, are operable independently with respect to the anchoring mechanism which attached the implant sockets to the implant head. Thus, the implant bar may be assembled, unassembled, replaced in part or in whole, etc. as required, and this may be accomplished on location by a dentist and/or technician, so as to reduce or eliminate the need for sub-contracting the manufacturing of the implant bar assembly. Moreover, the modular architecture of the implant bar system reduces waste of time, effort, material and costs due to errors or imprecision in the manufacturing process. Embodiments of the present invention are also advantageous in that the assembly, unassembly and adjusting of the dental implant bar system is executed quickly. Indeed and for indicative purposes, the applicant has assembled an implant bar system, according to a preferred embodiment of the present invention, on a model having 5 implants, in approximately one hour. Moreover, the above-mentioned assembly, unassembly and adjusting may be performed using simple tools that may be easily accessible and known to the dentist and/or technician in the field, for example, pliers, grippers, screw driver, etc. and the like. Alternatively, a matching set of tools may be manufactured for the specific use with the implant bar system, according to a preferred embodiment of the present invention. It is thus understood that other suitable tools may also be used and/or created for the purpose of manipulating the implant bar system according to a particular design, as can be easily understood by a person skilled in the art.

Several modifications could be brought to the above-described embodiments, as can be easily understood by a person skilled in the art. Indeed and for example, the collar opening described in the second embodiment may be replaced by any suitable shape which allows the socket to be fitted onto a corresponding implant head, as readily understood by a person skilled in the art. Moreover, the socket, telescopic arm may have a shape other than cylindrical.

Several other modifications could be made. Indeed, the bar assembly may comprise other suitable adjustable, pivotable and/or extendible bar systems, incorporating for example an elastic element such as a spring or rubber and/or comprising only one pivotable end and/or comprising a plurality of tubular segments. Moreover, the bar assembly may comprise any substantially elongated connector and may vary in profile, for example, rectangular, triangular, oval, etc. Furthermore, the articulation formed by the ball end and semi-spherical recess may be replaced by or incorporate a cylindrical hinge or system thereof. Moreover, the securing screws of the bar assembly may be replaced by other securing means such as a clip or any suitable fastening mechanism, without departing from the scope of the present invention, as can be easily understood by a person skilled in the art.

Furthermore, though the above described embodiments are directed to external dental implant bars, the present invention is also intended for subgingival applications, that is to say a dental implant system integrating the above described implant bar, at least a portion of the implant bar being located within the gingival tissue.

It will be understood that the above described embodiment is for purposes of illustration only and that changes and modifications may he made thereto without departing from the spirit and scope of the invention. Indeed, numerous modifications could be made to the above-described embodiments without departing from the scope of the invention, as apparent to a person skilled in the art.

The invention claimed is:

1. A dental implant bar for mounting on a set of prearranged implant heads for receiving dental implants, the dental implant bar comprising: a plurality of implant sockets for receiving the dental implants; an anchoring mechanism for fastening the sockets to the corresponding implant heads, each implant socket having an aperture therein for receiving the anchoring mechanism therethrough; at least one
    adjustable arm assembly, each arm assembly having opposite extremities and linking an adjacent pair of the implant sockets; and at least one compression assembly, each compression assembly holding, against the implant socket, one of the extremities of at least one of the at least one arm assembly linking the corresponding implant socket to an adjacent one of the implant sockets, the compression assembly being operable between a compressed configuration wherein each corresponding extremity is locked against the implant socket and a decompressed configuration wherein each corresponding extremity can swivel to change an orientation of the corresponding arm assembly with respect to the implant socket, each said anchoring mechanism being capable of removably fastening and unfastening a corresponding said implant socket to and from the corresponding implant head while the corresponding compression assembly is in the compressed configuration.

2. A dental implant bar according to claim 1, wherein each implant socket comprises a base having a top wall and a side wall, and a shaft projecting upwardly from the top wall of the base.

3. A dental implant bar according to claim 2, wherein the shaft has a threaded segment.

4. A dental implant bar according to claim 3, wherein each compression assembly comprises a tightening ring sized and shaped for mounting on the base and about the shaft of the implant socket and a nut for mating with the threaded segment of the shaft to hold the tightening ring against the base.

5. A dental implant bar according to claim 4, wherein the extremities of each arm assembly are substantially sphere-shaped.

6. A dental implant bar according to claim 5, wherein the implant socket defines a first-half recess therein and wherein the tightening ring of the corresponding compression assembly defines a second-half recess therein, the first-half and second-half recesses forming, when aligned, a substantially semispherical recess for receiving one of the extremities of said corresponding arm assembly.

7. A dental implant bar according to claim 5, wherein the implant socket defines a pair of opposed first-half recesses therein and the tightening ring defines a complementary pair of opposed second-half recesses therein, the first-half and second-half recesses forming, when aligned, a pair of substantially semispherical recesses for receiving therein corresponding extremities of two of the arm assemblies.

8. A dental implant bar according to claim 2, wherein the extremities of each arm assembly have a substantially annular shape, said extremities of the arm assemblies and the upper wall of the base of each implant socket having mating curved profiles.

9. A dental implant bar according to claim 2, wherein the implant socket is provided with a pair of locating apertures on the upper wall of the base and the tightening ring comprises a pair of locating pins extending from an underside thereof, the locating pins being configured to fit in the locating apertures of the implant socket.

10. A dental implant bar according to claim 2, wherein the implant socket comprises adjusting means.

11. A dental implant bar according to claim 10, wherein the adjusting means comprises a pair of opposed recesses provided in a lower portion of the base for allowing adjusting the implant bar via a gripping tool.

12. A dental implant bar according to claim 10, wherein the adjusting means comprises at least one opening provided in the base for receiving a corresponding adjusting tool, to adjust the implant bar.

13. A dental implant bar according to claim 2, wherein the base further defines a collar opening in the lower portion thereof for receiving the corresponding implant head.

14. A dental implant bar according to claim 1, wherein the arm assembly comprises a first arm segment and a second arm segment respectively projecting from said opposite extremities, and a central telescoping segment connecting said first and second arm segments in a telescopic cooperation.

15. A dental implant bar according to claim 14, wherein the first and second arm segments each have a threaded aperture extending transversally therein, said arm assembly further comprising a pair of set screws respectively received in said threaded apertures to frictionally lock the position of the first and second arm segments with respect to central telescopic segment.

16. A dental implant bar according to claim 1, wherein the arm assembly comprises an arm segment and a sleeve respectively projecting from said opposite extremities, said sleeve slidably receiving the arm segment therein.

17. A dental assembly according to claim 16, wherein said sleeve has a threaded aperture extending transversally therein, said arm assembly further comprising a set screw received in said threaded aperture to frictionally lock the position of the arm segment with respect to the sleeve.

18. A dental implant bar according to claim 1, wherein the arm assembly comprises a first arm segment and a second arm segment respectively projecting from said opposite extremities, the first and second arm segments being connected in a telescopic cooperation.

19. A dental implant bar according to claim 18, wherein at least one of the first and second arm segments has a threaded aperture extending transversally therein, said arm assembly further comprising a set screw received in said threaded aperture to frictionally lock the position of the first arm segment with respect to the second arm segment.

20. A dental implant bar according to claim 1, further including, for each implant socket, an adapter connecting to the respective implant socket and for operatively connecting with the corresponding implant head.

21. A dental implant system for receiving dental implants, the dental implant system comprising:
a set of prearranged implant heads; and a dental implant bar as claimed in claim 1, each implant socket of the dental implant bar being mounted on one of the prearranged implant heads.

22. The dental implant system according to claim 21, further comprising an anchoring mechanism including a connector provided on each implant head for receiving a corresponding one of the implant sockets, the connector defining a threaded bore; and a plurality of prosthetic screws, each for fitting through one of the implant sockets and mating with the threaded bore of the corresponding implant head to anchor said implant socket thereon.

* * * * *